(12) United States Patent
KenKnight et al.

(10) Patent No.: US 8,285,378 B1
(45) Date of Patent: Oct. 9, 2012

(54) SYSTEM AND METHOD FOR DETERMINING PATIENT-SPECIFIC IMPLANTABLE MEDICAL DEVICE PROGRAMMING PARAMETERS

(75) Inventors: Bruce KenKnight, Maple Grove, MN (US); Eric Lovett, Mendota Heights, MN (US); Adam W. Cates, Minneapolis, MN (US); Amir Tehrani, San Francisco, CA (US)

(73) Assignee: Cardiac Pacemakers, Inc, St. Paul, MN (US)

( * ) Notice: Subject to any disclaimer, the term of this patent is extended or adjusted under 35 U.S.C. 154(b) by 728 days.

(21) Appl. No.: 10/950,876

(22) Filed: Sep. 27, 2004

(51) Int. Cl.
*A61N 1/02* (2006.01)
(52) U.S. Cl. ........................................................ 607/30
(58) Field of Classification Search ................... 600/301, 600/510, 513, 523, 524; 607/30, 31, 59, 607/18
See application file for complete search history.

(56) References Cited

U.S. PATENT DOCUMENTS

| | | | |
|---|---|---|---|
| 5,690,690 A * | 11/1997 | Nappholz et al. | 607/30 |
| 6,024,699 A | 2/2000 | Surwit et al. | |
| 6,083,248 A | 7/2000 | Thompson | |
| 6,171,256 B1 | 1/2001 | Joo et al. | |
| 6,285,909 B1 * | 9/2001 | Sweeney et al. | 607/32 |
| 6,416,471 B1 | 7/2002 | Kumar et al. | |
| 6,478,737 B2 * | 11/2002 | Bardy | 600/301 |
| 6,665,558 B2 * | 12/2003 | Kalgren et al. | 600/510 |
| 6,827,670 B1 | 12/2004 | Stark et al. | |
| 6,970,741 B1 * | 11/2005 | Whitehurst et al. | 607/3 |
| 7,177,674 B2 * | 2/2007 | Echauz et al. | 600/544 |
| 2001/0011153 A1 * | 8/2001 | Bardy | 600/300 |
| 2002/0133206 A1 * | 9/2002 | Daum et al. | 607/14 |
| 2003/0097155 A1 * | 5/2003 | Stahmann et al. | 607/9 |
| 2004/0242972 A1 * | 12/2004 | Adak et al. | 600/300 |
| 2005/0192557 A1 * | 9/2005 | Brauker et al. | 604/503 |
| 2005/0234356 A1 * | 10/2005 | Rowlandson et al. | 600/510 |

OTHER PUBLICATIONS

E. Braunwald, "Heart Desease—A Textbook of Cardiovascular Medicine," Ch. 5, pp. 153-176, Ch. 15, pp. 445-470, W.B. Saunders Co., 5th ed. (1997).

* cited by examiner

*Primary Examiner* — Scott Getzow
*Assistant Examiner* — Amanda Patton
(74) *Attorney, Agent, or Firm* — Pauly, DeVries Smith & Deffner LLC (57) ABSTRACT

A system and method for determining patient-specific implantable medical device programming parameters are presented. A set of physiological measures collected through a plurality of sensors monitoring physiological functions in a patient are assimilated. The physiological measures set are analyzed to identify physiological idiosyncrasies specific to the patient and to optimize the therapy to be delivered through an implantable medical device. A patient profile is formed including a plurality of programming parameters and the patient profile is preprogrammed into the implantable medical device prior to implantation in the patient.

14 Claims, 8 Drawing Sheets

SYSTEM AND METHOD FOR DETERMINING PATIENT-SPECIFIC IMPLANTABLE MEDICAL DEVICE PROGRAMMING PARAMETERS

FIELD OF THE INVENTION

The present invention relates in general to implantable medical devices and, in particular, to a system and method for determining patient-specific implantable medical device programming parameters.

BACKGROUND OF THE INVENTION

Currently, implantable medical devices (IMDs) are trending towards providing advanced patient management features that enable health care providers to more closely tailor therapy to meet increasingly particularized patient needs. For instance, based on patient-specific data, health care providers can form a clinical trajectory of projected treatment outcome or generate a wellness indicator to provide both a snapshot reading of patient status and in use in creating a trending analysis. Such patient-specific data can also be used for providing blended sensor optimization, AV interval delay optimization, arrhythmia prediction, and similar IMD-specific programming.

Conventional IMD programming relies primarily upon population-based data. IMD candidate patients are medically evaluated and broadly characterized using well-known sets of classifications, which include, for example, the New York Heart Association (NYHA) classifications, described in E. Braunwald, ed., "Heart Disease—A Textbook of Cardiovascular Medicine," Ch. 15, pp. 445-470, W.B. Saunders Co. ($5^{th}$ ed. 1997), the disclosure of which is incorporated by reference. Evaluation can include physical stressors, such as described in Ibid. at Ch. 5, pp. 153-176, pharmacological stressors, as well as sensory or autonomic, or metabolic stressors to establish a diagnosis by determining cardiopulmonary functional capacity and to estimate a treatment prognosis.

IMD programming based on population-based data, at best, provides a starting point that requires further refinement to tailor therapy to a recipient patient. Classifications are helpful as an aid to providing an initial set of parameters, but potentially overlook patient-specific features available on a specific IMDs. Additionally, further ad hoc fine tuning during or following surgery is often necessary to eventually arrive at a suitable parameter set. Conversely, patient-specific data, when available, can assist a healthcare provider in defining parameters based on a variety of conditions or situations not routinely factored into parameters selection. For instance, the AV delay in patients indicated for pacing therapy may be initially optimized by maximizing cardiac output at rest, but how the AV delay is programmed to change during exercise is based on population-based data. Historical data from a patient's exercise test conducted prior to the development of Bradycardia indications could be useful for determining the optimal AV delay over a range of physiologically relevant heart rates.

Similarly, IMDs with advanced patient management features generally require learning periods to observe the patient, during which the advanced features are either unavailable or less effective. Such programming changes based solely on empirically-observed data frequently fail to factor in extrinsic predictive markers of disease state, such as family history, current medications, and so forth. Moreover, any reference baseline generated during the learning period post facto may be artificially skewed by the therapeutic effect of the device.

Therefore, there is a need for an approach to preprogramming an IMD or other medical device based on physiological measures and evaluated prior to implantation to pre-seed operational values based on a patient-specific analysis of the physiological measures.

SUMMARY OF THE INVENTION

A system and method for determining patient-specific implantable medical device programming parameters. A set of physiological measures collected through a plurality of sensors monitoring physiological functions in a patient are assimilated. The physiological measures set are analyzed to identify physiological idiosyncrasies specific to the patient and to optimize the therapy to be delivered through an implantable medical device. A patient profile is formed including a plurality of programming parameters and the patient profile is preprogrammed into the implantable medical device prior to implantation in the patient.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

System Overview

Figure 1:
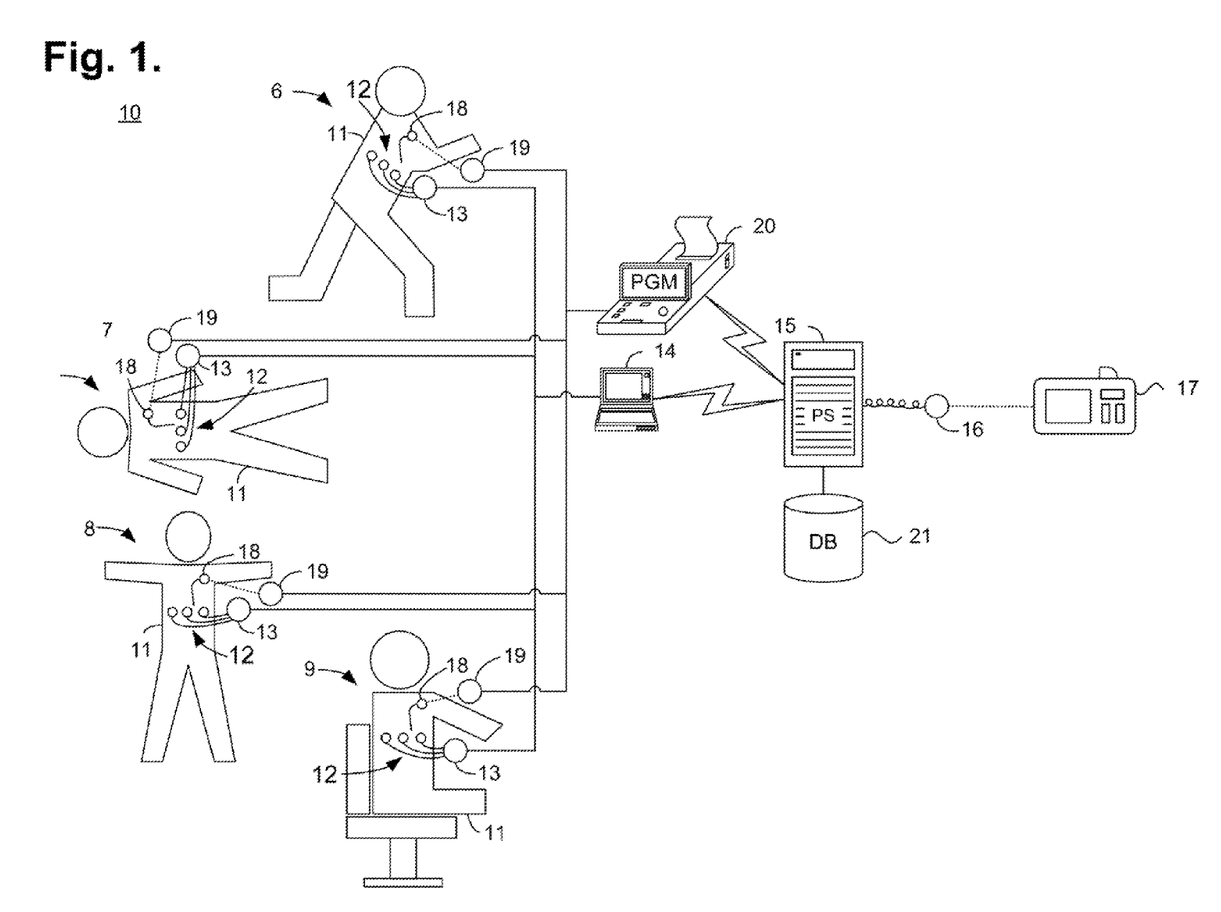
FIG. 1 is a block diagram showing a system for determining patient-specific implantable medical device programming parameters, in accordance with an embodiment of the invention.

FIG. 1 is a block diagram 10 showing a system for determining patient-specific implantable medical device programming parameters, in accordance with an embodiment of the invention. A patient 11 is monitored by a plurality of external sensors 12, such as a Holter heart monitor or conventional 12-lead electrocardiograph 14, or by sensors provided through an implanted medical device 18, such as implemented in cardiac pacemakers used for managing bradycardia, implantable cardioverter defibrillators used for treating tachycardia, and other types of implantable cardiovascular monitors and therapeutic devices used for monitoring and treating heart failure, structural problems of the heart, such as congestive heart failure, rhythm problems, and other heart conditions, as would be appreciated by one skilled in the art. Examples of cardiac pacemakers suitable for use in the described embodiment include the Pulsar Max II, Discovery, and Discovery II pacing systems, sold by Guidant Corporation, St. Paul, Minn. An example of an implanted medical device 18 suitable for use in the described embodiment includes the Contak Renewal cardiac resynchronization therapy defibrillator, also sold by Guidant Corporation, St. Paul, Minn.

The patient 11 is monitored while engaged in performing a prescribed set of timed physical stressors during an initial observation period. The timed physical stressors are a set of normal patient activities and cardiovascular and respiratory maneuvers that allow consistent, reproducible physiological functions to be measured. These maneuvers include activities, such as a change in posture, simple physical exercises, oxygen challenges, and breathing state, including holding breath and hyperventilating. By way of example, the stressors include timed physical activities, such as running in place 6, recumbency 7, standing 8, and sitting motionless 9.

By way of example, an illustrative prescribed set of timed physical stressors for a non-ambulatory patient 11 is as follows:

(1) Running in place 6: if possible, the patient 11 must run in place for about five minutes;
(2) Walking (not shown): if possible, the patient 11 must walk for about six minutes and the total distance walked is measured;
(3) Ascending stairs (not shown): if possible, the patient 11 must ascend two flights of stairs;
(4) Recumbency 7: if possible, the patient 11 must recline following about two minutes of motionless immobile upright posture. Upon recumbency, the patient 11 must remain as immobile as possible for about ten minutes;
(5) Standing 8: if possible, the patient 11 must briskly assume an upright standing posture after the ten-minute recumbency 7 and must remain standing without activity for about five minutes;
(6) Coughing (not shown): if possible, the patient 11 must cough forcefully about three times when in an upright position to record cardiovascular pressures;
(7) Hyperventilation (not shown): if possible, the patient 11 must hyperventilate over thirty seconds with full deep and rapid breaths to record ventilatory status;
(8) Sitting motionless 9: when a physician is complicit, the patient 11 must, if possible, use an approximately 2.0 liter per minute nasal cannula while transmitting data for about twenty minutes while sitting to evaluate cardiopulmonary response;
(9) Program AAI and VVI temporary pacing interventions for five minutes, at low and high rates, if applicable, for instance, 40 bpm and 120 bpm, to evaluate cardiopulmonary response; and
(10) Test dual site or biventricular pacing modes, if applicable, for approximately twenty minutes to evaluate cardiopulmonary response.

Stressors (9) and (10) require an invasive procedure to surgically implant a medical device capable of providing the applicable pacing modes and measurements. Other timed physical stressors are possible, as would be appreciated by one skilled in the art. Other physical stressors include, by way of examples, a treadmill test, Valsalva maneuver, sleep, particularly REM sleep, and normal ambulation. The patient 11 can also challenged by pharmacological stressors, such as phenylephrine or atropine, sensory or autonomic stressors, such as cold pressor, or metabolic stressors, such as glucose. Other types of stressors in addition to or in lieu of physical, pharmacological, sensory or autonomic, and metabolic stressors are possible. In a further embodiment, the patient 11 can be reassessed while performing the timed physical stressors during subsequent observation periods or while being influenced by further pharmacological, sensory or autonomic, or metabolic stressors.

In the described embodiment, the physical and pacing stimulus stressors must be annotated with date and time of day correlated with symptoms and, in a further embodiment, quality of life (QOL) measures. Heart rate, temperature, and time of day are directly measured while the patient activity score and cardiac output score are derived from collected quantitative physiological measures. The physical stressors are merely illustrative in nature and the set of timed physical and pacing stimulus stressors actually performed by any given patient would necessarily depend upon age and physical condition as well as the type and capabilities of the medical device to be implanted.

In a further embodiment, the quantitative physiological measures in the reference baseline are reassessed on a periodic basis, such as annually or quarterly. In addition, if the quantitative physiological measures were recorded during a period when the patient 11 was unstable or recovering from a recent illness, the reference baseline is reassessed when the patient 11 is again stable.

The external sensors 12 record quantitative physiological measures, which are received by a set of leads 13. The leads 13 are connected to a standard twelve-lead electrocardiograph 14 or similar physiological measuring device or monitor. The electrocardiograph 14 collects sets of the quantitative physiological measures and provides the collected measures to a programming server 15 for storage in a database 21.

Similarly, the implanted medical device 18 records and temporarily stores quantitative physiological measures, which are retrieved by a programmer 20 or similar device through a wand 19 placed over the location of the implanted medical device 18. Programming or interrogating instructions can also be sent to the implanted medical device 18. Any form of programmer, interrogator, recorder, monitor, or telemetered signals transceiver suitable for communicating with the implanted medical device 18 could be used, as would be appreciated by one skilled in the art. The programmer 20 provides the sets of quantitative physiological measures to the programming server 15 for storage in the database 21. An example of a programmer suitable for use in the present invention is the Model 2910 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device, as would be appreciated by one skilled in the art.

Upon receiving the sets of quantitative physiological measures, the programming server 15 assimilates the physiological measures with other measures in the database 21, including QOL measures, and analyzes the collected measures to form programming parameters, diagnoses and prognoses, as further described below with reference to FIG. 4. The prognostication is based on epidemiologic and population data also contained in the database 21. The quantitative physiological measure analyses can be used to create a patient profile containing programming parameters for an implantable medical device (MD) 17, such as a pacemaker, cardiac resynchronization therapy pacemaker, implantable cardioverter defibrillator, cardiac resynchronization therapy defibrillator, neurostimulation device, and implantable drug pump. In a further embodiment, the programming server 15 interfaces to a programming wand 16 for preprogramming the IMD 17 prior to implantation based on a patient-specific set of operational parameters. In a still further embodiment, the patient profile is downloaded to a programmer (not shown), such as a Model 2910 programmer recorder monitor, manufactured by Guidant Corporation, St. Paul, Minn., also for preprogramming the IMD 17 prior to implantation in the patient.

The programming server 15 includes a general purpose, programmed digital computing device, including a central processing unit, random access memory, non-volatile secondary storage, such as a hard drive or CD ROM drive, network or wireless interfaces, and peripheral devices, including user interfacing means, such as a keyboard and display. Program code, including software programs, and data are loaded into the RAM for execution and processing by the CPU and results are generated for display, output, transmittal, or storage.

Process Flow

Figure 2:
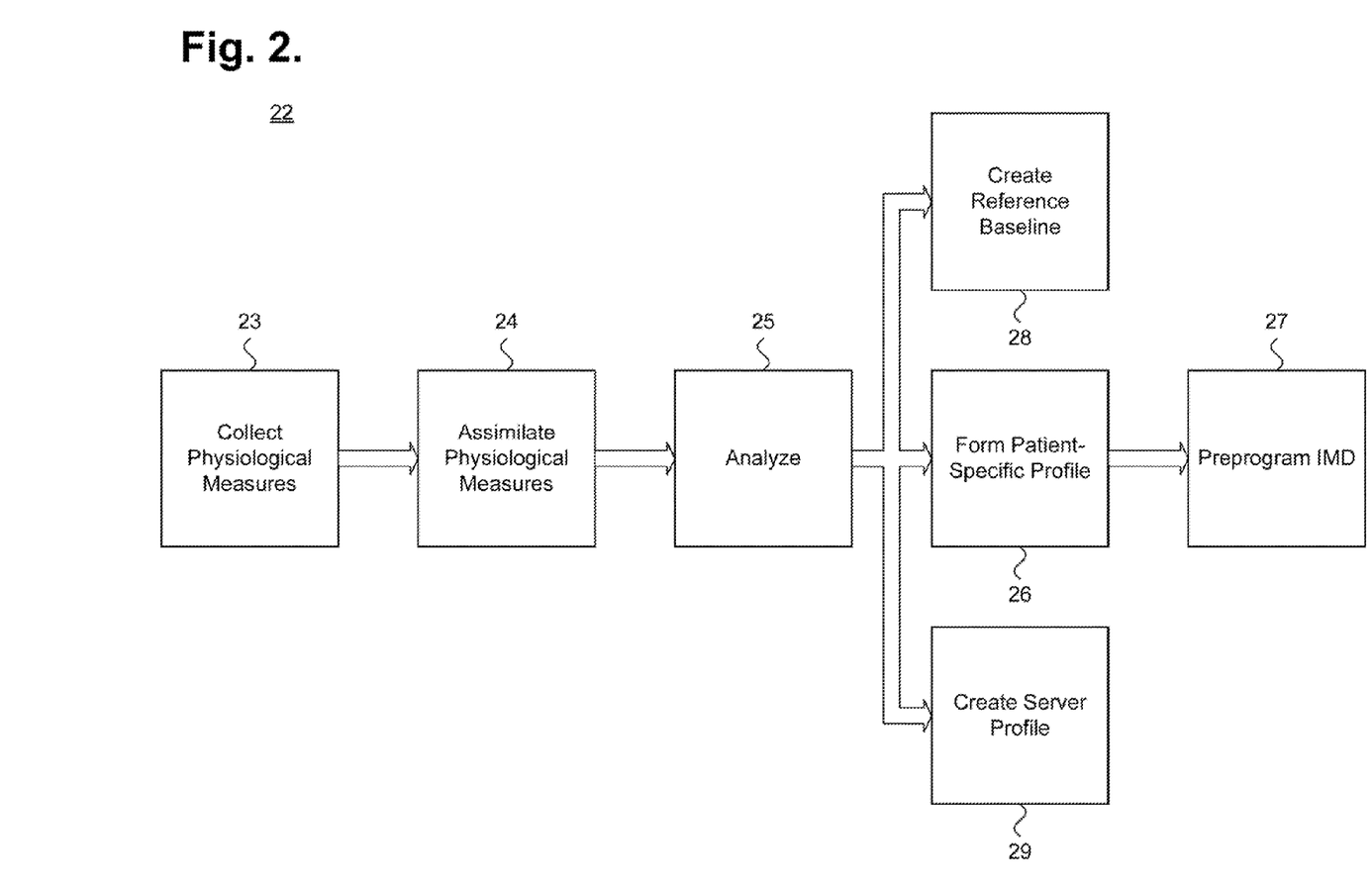
FIG. 2 is a process flow diagram showing the operations followed to form programming parameters and related analyses according to one embodiment of the invention.

FIG. 2 is a process flow diagram 22 showing the operations followed to form programming parameters and related analyses according to one embodiment of the invention. The process is performed on a patient-specific basis to enable healthcare providers to customize the features implemented in an IMD 17 with "pre-seeded" values prior to implantation. Quantitative physiological measures are collected (operation 23), through external measurement means, such as a standard twelve-lead electrocardiograph, or through internal measurement means, such as provided through sensors coupled to an implanted medical device. The quantitative physiological measures can be associated with a suitable set of timed physical stressors performed by the patient during physiological measures collection, with non-timed physical stressors, with pharmacological, sensory or autonomic, or metabolic challenges, or by a combination of the foregoing stressors and challenges.

The quantitative physiological measures are assimilated into the database 21 (operation 24). In a further embodiment, the quantitative physiological measures are assimilated into the database 21 with QOL and related qualitative measures. Assimilation converts, normalizes and derives further measures. Non-electrocardiographic observations can be included in the database 21, such as blood pressure, post-exercise systolic blood pressure ratios, maximum work capacity, sub-maximal exercise, heart rate response, rate-pressure product and chest discomfort, to assist in identifying co-morbidities and other health disorders. In addition, epidemiologic and population data can be included in the database 21 for use in generating a prognostication. The assimilated measures are then analyzed (operation 25) to diagnose a patient health status and to prognosticate a clinical trajectory for consideration during therapy provided by the IMD 17. Diagnostically, the assimilated measures can, for example, reveal a severity of ischemic response, provide correlation of exercise test results with coronary angiography, or identify markers indicative of coronary disease. Prognostically, standard evaluative and statistical analyses can be applied to predict a potential outcome based on therapy delivered through an IMD 17, as would be appreciated by one skilled in the art. Diagnosis and prognostication relative to cardiac disease is further described in Ibid. at Ch. 5, pp. 153-176, the disclosure of which is incorporated by reference.

Following analysis, the assimilated measures can be formed into a patient-specific profile (operation 26) for use in preprogramming an IMD 17 (operation 27). Additionally, the assimilated measures can be used to create a reference baseline (operation 28) or a server profile (operation 29), which respectively reflect the initial patient health status in physiological terms and IMD programming parameters in parametric terms.

By way of example, IMD preprogramming can be used to generate customized programming parameter sets based on patient-specific data, such as generated through the physical, pharmacological, sensory or autonomic, or metabolic stressor challenges, as further described above with reference to FIG. 1. Preprogramming examples non-exclusively include:

(1) Rate adaptive cardiac resynchronization therapy (CRT): Pacing rate, AV delay, interventricular delay, LA-LV delay, and related parameters can be pre-customized based on physical stressor and echocardiogram or pharmacological, in particular, phenylephrine, stressors and echocardiogram assessments for use in therapy for congestive heart failure caused by dilated cardiomyopathy.

(2) Optimal AV delay: AV delay can be pre-customized for patients indicated for cardiac pacing and CRT.

(3) Anti-oversensing: parameters and algorithms can be pre-customized to avoid oversensing. For example, observed T-wave morphology might be sporadic with periods of large amplitude T-waves commonly occurring. Employing pre-implant chronic empirical data could enable the preprogramming of an optimal sensitivity level for amplifiers to minimize T-wave oversensing.

(4) Arrhythmia prediction: parameters and algorithms to predict future events can be pre-customized based on observed cycle lengths leading up to ventricular tachycardia unique to a specific patient.

(5) Rate-adaptive pacing profile: parameters can be pre-customized based on historical data for chronotropically incompetent patients.

(6) Postural-adaptive pacing: parameters, in particular, pacing parameters, can be pre-customized in response to a postural shift, rather than waiting for a rate-drop in patients suffering from orthostatic hypotension.

Example Database Schema

Figure 3:
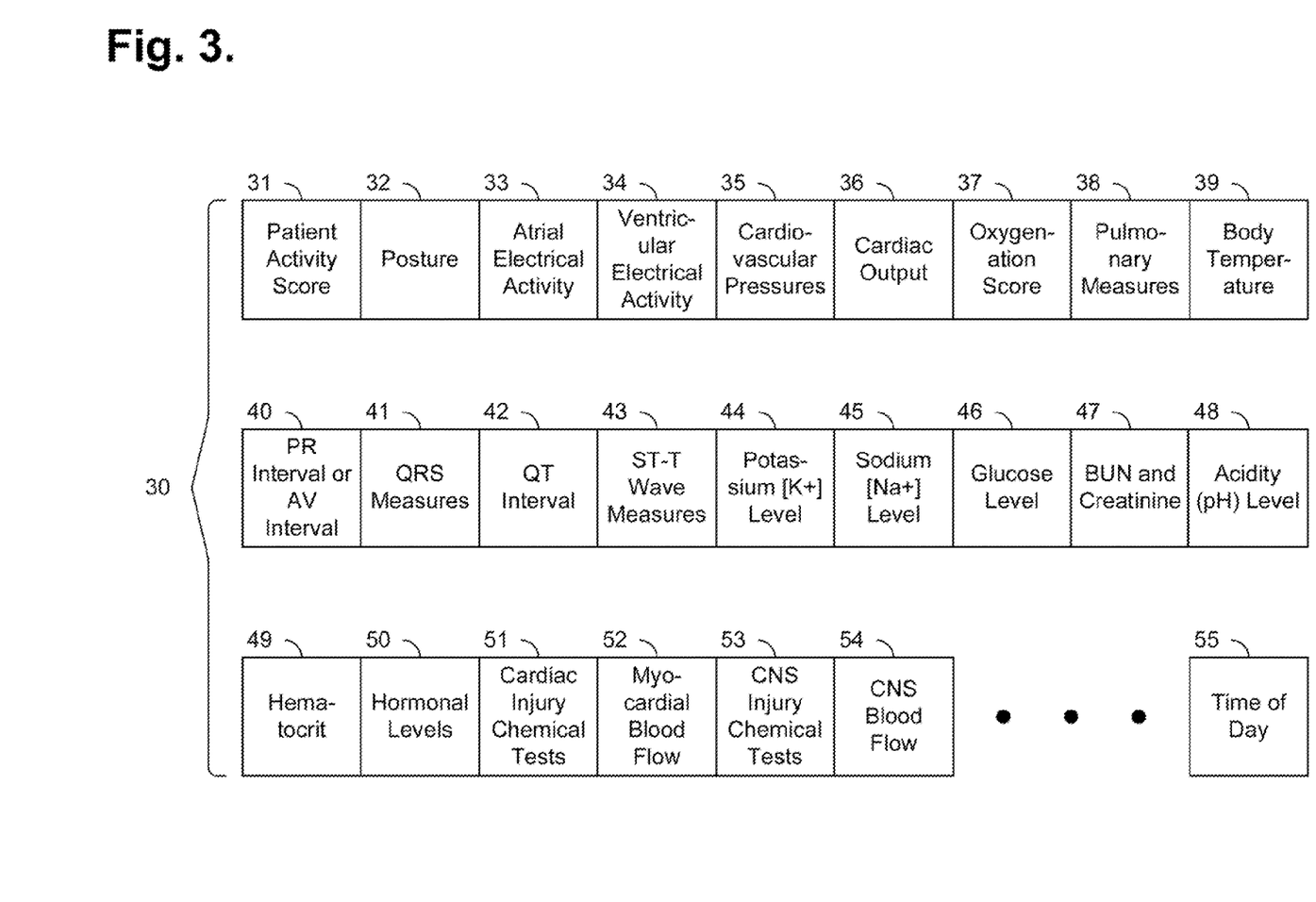
FIG. 3 is a database schema showing, by way of example, the organization of a reference baseline for cardiac patient care for use in the system of FIG. 1.

FIG. 3 is a database schema showing, by way of example, the organization of a reference baseline 30 for cardiac patient care for use in the system 10 of FIG. 1. The reference baseline 30 chronicles the health status of a patient 11 prior to receiving an implant of an IMD 17 and provides an objective basis upon which the patient-specific programming for the IMD 17 is based.

For example, for a cardiac patient, the reference baseline 30 non-exclusively stores the following quantitative physiological measures and non-physiological measures: patient activity score 31; posture 32, such as through the use of one or more triaxial accelerometers; atrial electrical activity 33, such as atrial rate; ventricular electrical activity 34, such as ventricular rate; cardiovascular pressures 35; cardiac output 36; oxygenation score 37, such as mixed venous oxygenation; pulmonary measures 38, such as transthoracic impedance, measures of lung wetness, or minute ventilation; body temperature 39; PR interval 40, or AV interval; QRS measures 41, such as width, amplitude, frequency content, or morphology in the form of representative complexes or templates; QT interval 42; ST-T wave measures 43, such as T wave alternans or ST segment depression or elevation; potassium level 44; sodium level 45; glucose level 46; blood urea nitrogen and creatinine 47; acidity level 48; hematocrit level 49; hormonal levels 50, such as insulin or epinephrine; cardiac injury chemical tests 51, such as troponin or myocardial band creatinine kinase; myocardial blood flow 52; central nervous system injury chemical tests 53, such as cerebral band creatinine kinase; central nervous system blood flow 54; and time of day 55. Other types of measures or information are possible, such as a record of genetic information and gene expression. In addition, a well-documented set of derived measures can be determined based on the quantitative physiological measures and non-physiological measures, as would be appreciated by one skilled in the art.

In a further embodiment, QOL measures can be recorded to augment the quantitative physiological measures with a patient's self-assessment of physical and emotional well-being. Preferably, each QOL measures set is recorded substantially contemporaneous to the collection of an identified set of quantitative physiological measures. The date and time of day at which the QOL measures set was recorded can be used to correlate the QOL measures set to the quantitative physiological measures set recorded closest in time.

The pairing of the QOL measures set and an identified quantitative physiological measures set provides health care providers with a more complete picture of the patient's medical status by combining physiological "hard" machine-recorded data with semi-quantitative "soft" patient-provided data. A QOL measure is a self-assessment of an individual patient's physical and emotional well being and a record of symptoms, such as provided by the Duke Activities Status Indicator. These scoring systems can be provided for use by a patient 11 to record his or her QOL scores for both initial and periodic download to the programming server 16.

Other types of QOL and symptom measures are possible, such as those indicated by responses to the Minnesota Living with Heart Failure Questionnaire described in Ibid. at Ch. 15, pp. 445-470, the disclosure of which is incorporated by reference. Similarly, functional classifications based on the relationship between symptoms and the amount of effort required to provoke the symptoms can serve as QOL and symptom measures, such as the New York Heart Association (NYHA) classifications I, II, III and IV, also described in Ibid.

Programming Server

Figure 4:
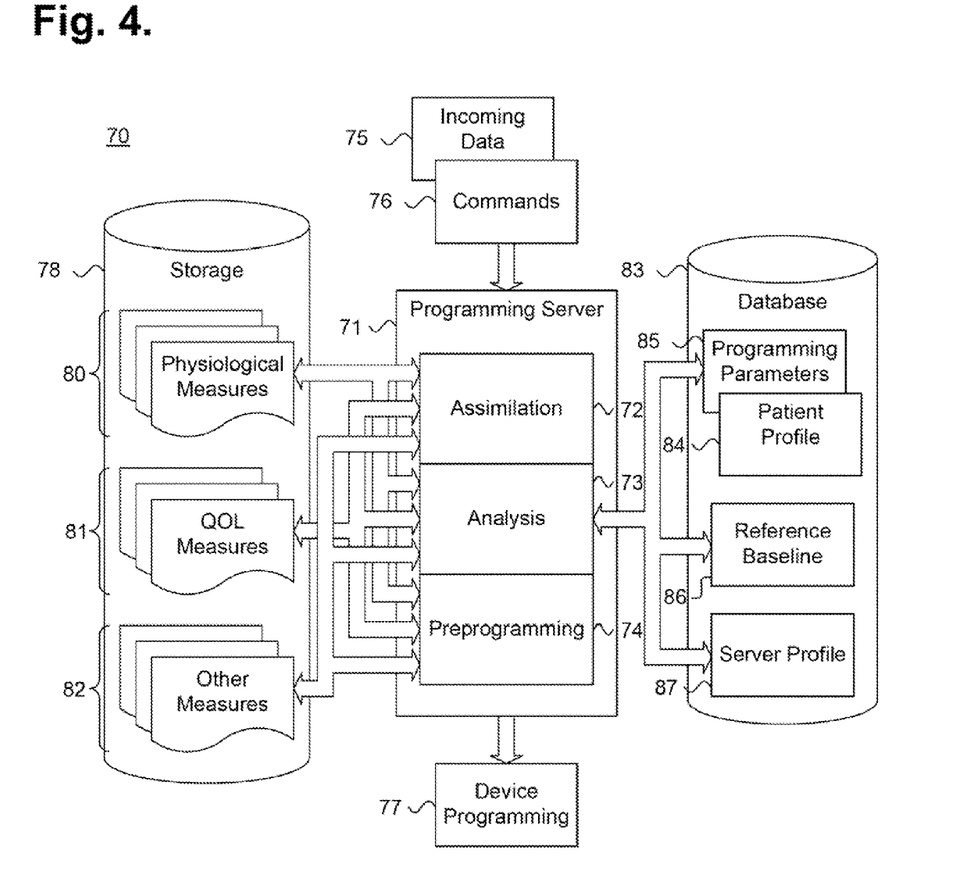
FIG. 4 is a functional block diagram showing a programming server for use in the system of FIG. 1.

FIG. 4 is a functional block diagram 70 showing a programming server 71 for use in the system 10 of FIG. 1. The programming server 71 receives incoming data 75 and commands 76 and generates device programming 77. The incoming data 75 includes raw quantitative physiological measures 80, as well as QOL measures 81 and other measures 82. The various measures are maintained in a storage device 78 coupled to the programming server 71. The commands 76 include instructions to generate a patient profile 84, programming parameters 85, reference baseline 86, and server profile 87, which are maintained in a database 83 also coupled to the programming server 71.

Programming server 71 includes an assimilation module 72, analysis module 73, and preprogramming module 74. The assimilation module 72 receives the physiological measures 80, QOL measures 81, and other measures 82 and processes each of the types of respective measures into normalized, derived, qualified, and quantified measures, as appropriate. For example, the physiological measures 80 are initially received as raw ECG signals, which must be correlated to heart interval and function. The analysis module 73 evaluates the physiological measures 80, QOL 81 and other measures 82 to form a patient profile 84, which is maintained in a database 83. The patient profile 84 identifies the physiological idiosyncrasies of and optimizes existing therapies for a particular patient. The patient profile 84 can also capture the patient health status diagnosis of the patient and can include a clinical trajectory as a prognosis of possible outcome for the course of therapy through an IMD 17. The preprogramming module 74 generates a set of programming parameters 85 based on the patient profile 84, which is output as device programming 77.

Method Overview

Figure 5:
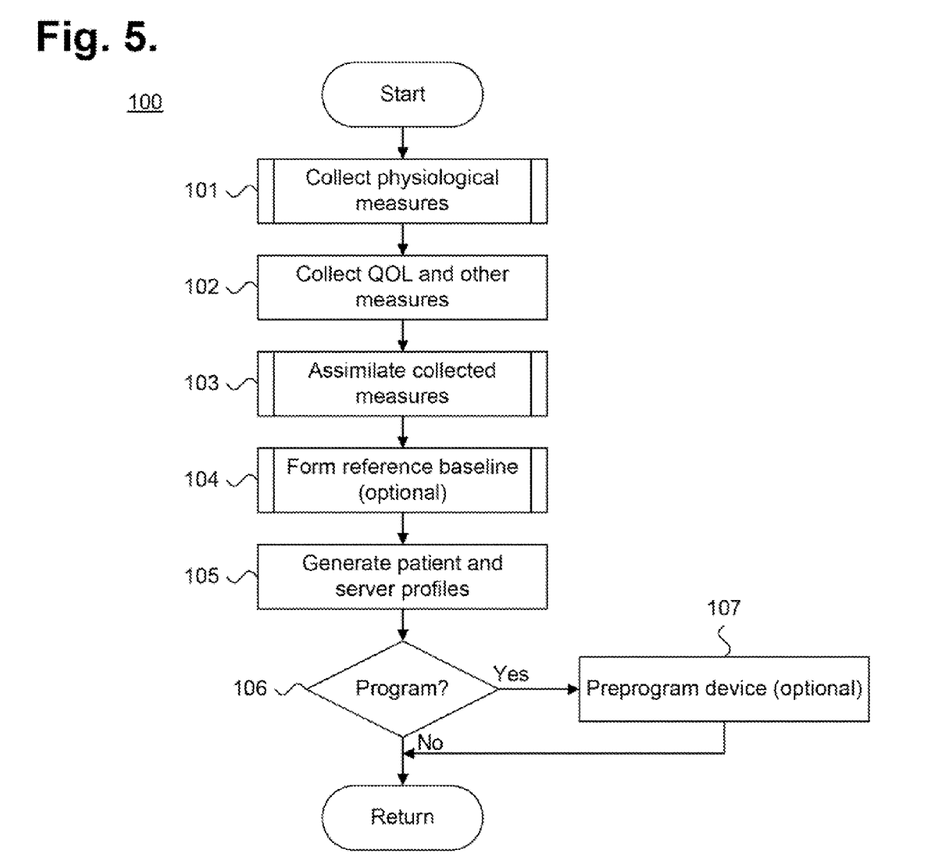
FIG. 5 is a flow chart showing a method for determining patient-specific implantable medical device programming parameters, in accordance with an embodiment of the invention.

FIG. 5 is a flow chart showing a method 100 for determining patient-specific implantable medical device programming parameters, in accordance with an embodiment of the invention. The method 100 is described as a sequence of process operations or steps, which can be executed by the programming server 71.

As an initial step, the programming server 71 collects physiological measures 80 (block 101), as further described below with reference to FIG. 6. If available, the programming server 71 also collects QOL measures 81 and other measures 82 (block 102), which are then assimilated together with the quantitative physiological measures 80 (block 103), as further described below with reference to FIG. 7. The assimilated measures can optionally be formed into a reference baseline 86 (block 104), as further described below with reference to FIG. 8. A patient profile 84, including programming parameters 85, and an optional server profile 87 are generated (block 105). to identify the physiological idiosyncrasies of and optimize existing therapies for a particular patient. Finally, upon generating the set of programming parameters 85 (block 106), the programming server 71 optionally preprograms the IMD 17 based on the set of programming parameters 85 (block 107), such as through short range telemetry, as would be appreciated by one skilled in the art. The routine then terminates.

Physiological Measures Collection

Figure 6:
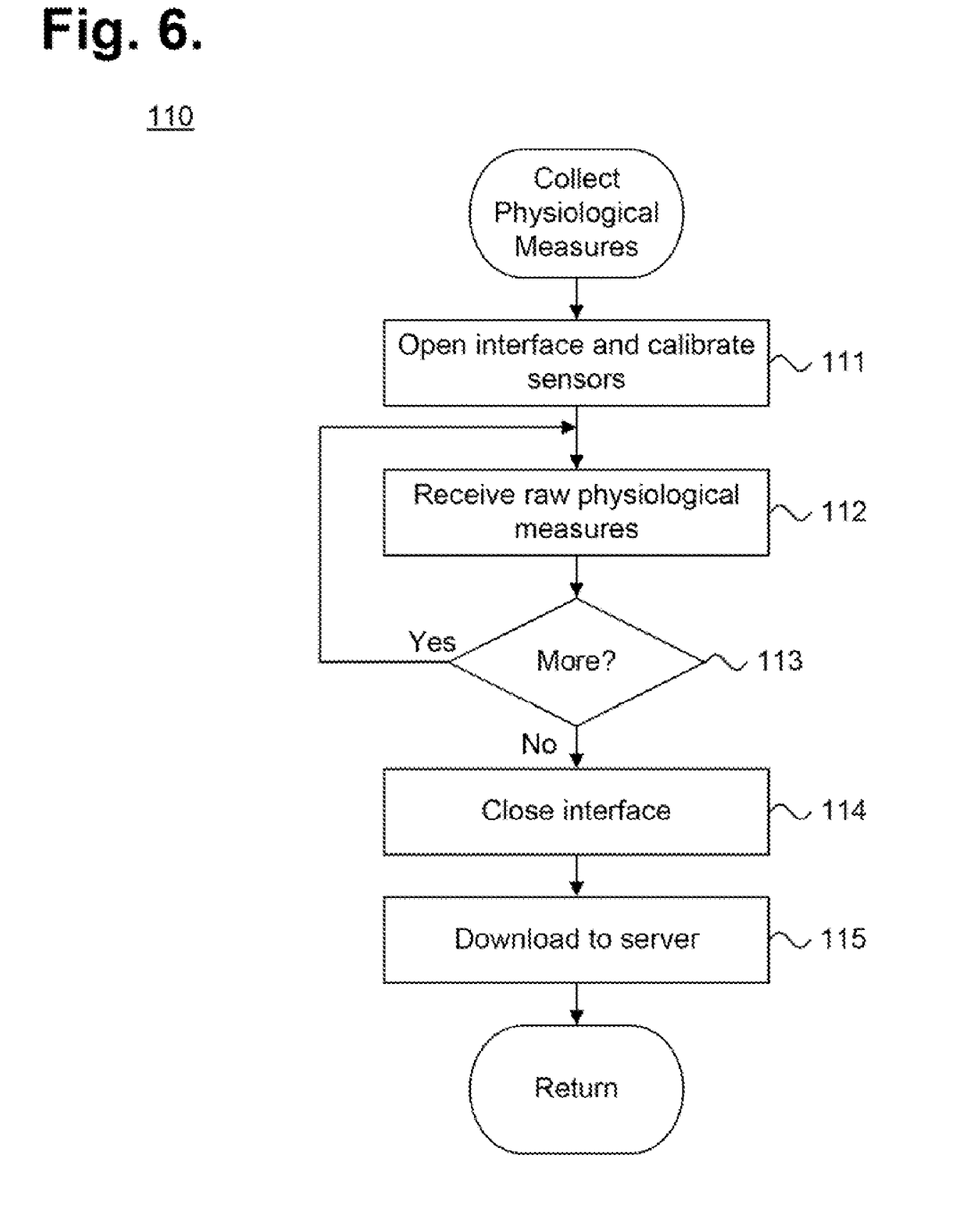
FIG. 6 is a flow chart showing a routine for collecting physiological measures for use in the method of FIG. 5.

FIG. 6 is a flow chart showing a routine 110 for collecting physiological measures 80 for use in the method 100 of FIG. 5. The purpose of the routine is to physically collect a set of quantitative physiological measures 80 from an electrocardiograph 14, programmer 20, or similar physiological measuring device.

Initially, an interface to the electrocardiograph 14 is opened and the sensors 12 are calibrrated (block 111). Alternatively, an interface to the implanted medical device 18 is opened using a wand 19 coupled to a programmer 20. Raw physiological measures are received into the electrocardiograph 14 or programmer 20 (block 112), which continues to receive additional raw physiological measures throughout the period of observation (block 113). The interface to the electrocardiograph 14 or programmer 20 is then closed (block 114) and the collected raw physiological measures are downloaded to the programming server 71 (block 115). The routine then returns.

Collected Measures Assimilation

Figure 7:
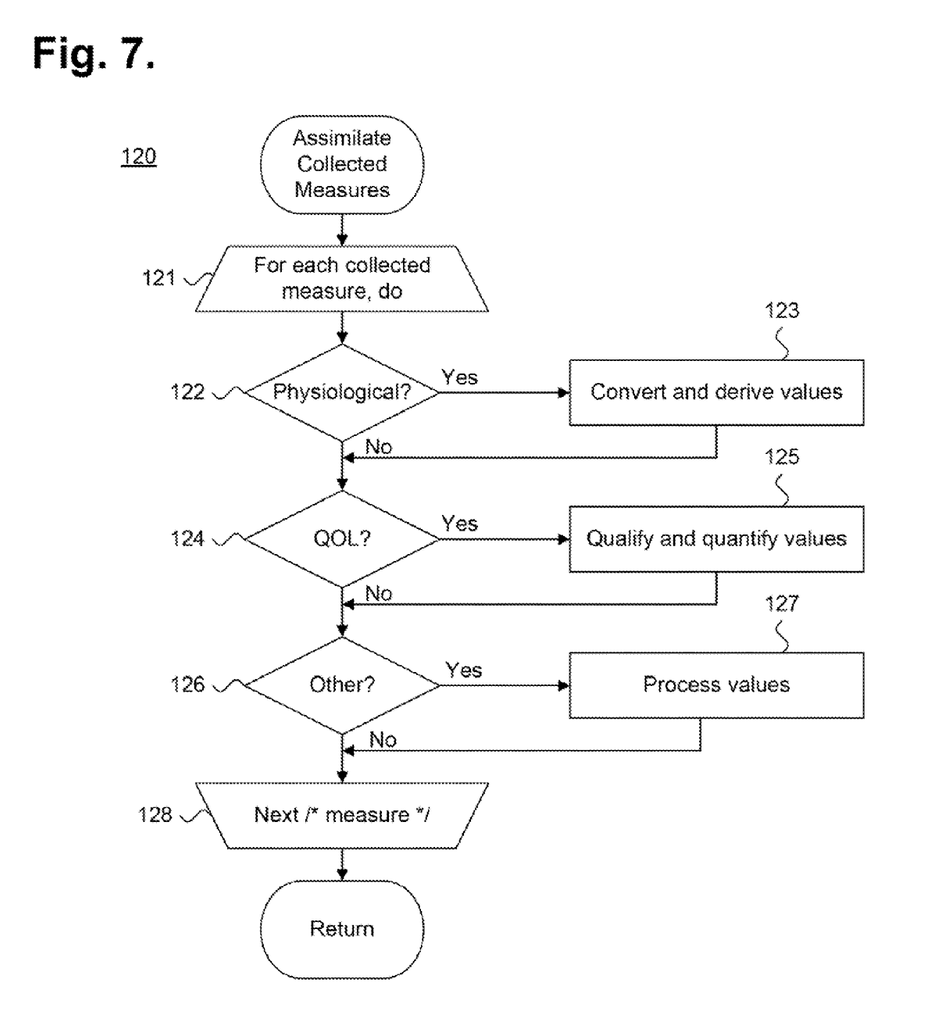
FIG. 7 is a flow chart showing a routine for assimilating collected measures for use in the method of FIG. 5.

FIG. 7 is a flow chart showing a routine 120 for assimilating collected measures for use in the method 100 of FIG. 5.

The purpose of the routine is to preprocess the various measures received as incoming data 75 for use during analysis to diagnose a patient health status and to prognosticate a clinical trajectory for consideration during therapy provided by the IMD 17.

Each collected measure is iteratively processed (blocks 121-122) as follows. During each iteration (block 121), if the collected measure is a quantitative physiological measure (block 122), the measure is converted and derived (block 123) to correlate to an associated heart interval and function. If the collected measure is a QOL measure 81 (block 124), the measure is qualified and quantified based on a standardized criteria (block 125), such as described above with reference to FIG. 3. Finally, all other measures (block 126) are processed as appropriate and stored (block 127). For instance, the time of day 55 is matched to the appropriate quantitative physiological measures 80 to match the time of the physical stressor being performed when the measure was collected. Each remaining collected measure is processed (block 120), after which the routine returns.

Reference Baseline Formation

Figure 8:
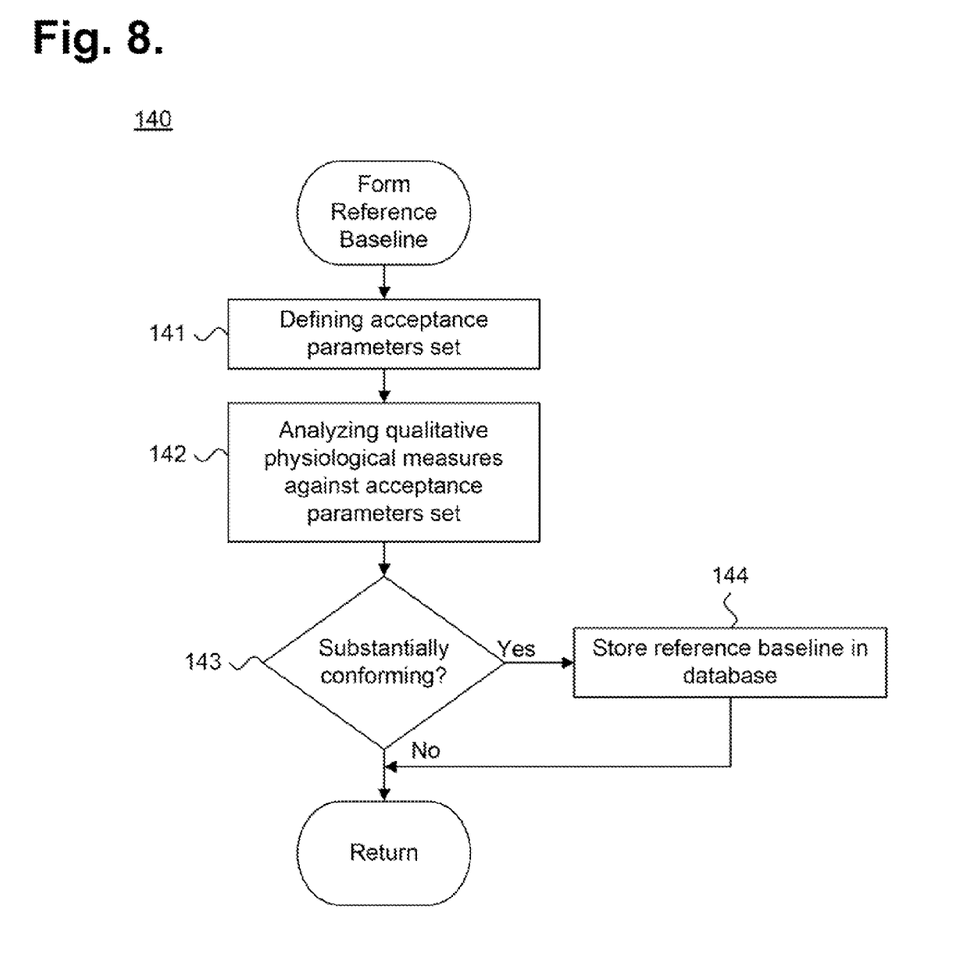
FIG. 8 is a flow chart showing a routine for forming a reference baseline for use in the method of FIG. 5.

FIG. 8 is a flow chart showing a routine 140 for forming a reference baseline 86 for use in the method 100 of FIG. 5. The purpose of the routine is to form the reference baseline 86 based on the quantitative physiological measures 80, qualitative measures, such as QOL measures, and other measures, to reflect a patient status prior to the implantation of an IMD 17.

Initially, a set of acceptance parameters is defined (block 141). The acceptance parameters provide an indication of those patients for whom automated patient-specific programming may not be appropriate based on an analysis of the quantitative physiological, qualitative, and other measures. For instance, an acceptance parameter for heart rate might be specified as a mean heart rate within a range of 40-90 beats per minute (bpm) over a 24-hour period. However, a patient with quantitative physiological measures falling either substantially above or below this acceptance parameter, for example, in excess of 90 bpm, would be considered substantially non-conforming and may be recommended for manual programming by the responsible healthcare provider. Thus, each quantitative physiological measure 80 is analyzed against the acceptance parameter set (block 142). The acceptance parameters are those indicator values consistent with the presence of some form of chronic yet stable disease, which does not require immediate emergency care. In the described embodiment, the acceptance parameters set for the reference baseline 86 are, by way of example, as follows: cardiac output 36 falling below 2.5 liters/minute/m$^2$; heart rate below 40 bpm or above 120 bpm; body temperature 39 over 101° F. and below 97° F.; patient activity 31 score of 1.0 or below; oxygenation score 37 of less than 60% mixed venous saturation at rest; pulmonary artery diastolic pressure greater than 20 mm Hg at rest; and minute ventilation less than 10.0 liters/minute at rest. Other acceptance parameters in addition to or in lieu of the foregoing acceptance parameters are possible, as would be appreciated by one skilled in the art. Those quantitative physiological measures 80 that substantially conform to the acceptance parameters (block 143) are stored in the reference baseline 86 (block 144). The routine then returns.

While the invention has been particularly shown and described as referenced to the embodiments thereof, those skilled in the art will understand that the foregoing and other changes in form and detail may be made therein without departing from the spirit and scope of the invention.

What is claimed is:

1. A method for determining patient-specific implantable medical device programming parameters, comprising:
   prior to implant of a patient-specific implantable medical device, collecting physiological measures through a plurality of external sensors monitoring reference baseline physiological functions in a patient candidate;
   receiving a self-assessment of physical and emotional well-being from the patient candidate;
   forming a patient profile factored on the physiological measures and the self-assessment, wherein the self-assessment correlates with the physiological measures collected;
   optimizing a therapy by a programming server to be delivered through the patient-specific implantable medical device not yet implanted in the patient candidate by evaluating the patient profile, comprising:
      determining a patient health status from the patient profile;
      prognosticating a clinical trajectory predicted as an outcome of the therapy; and
      generating customized programming parameter sets by the programming server for the therapy based on the physiological measures and the self-assessment;
   preprogramming the implantable medical device with the therapy comprised of the customized programming parameter sets into the implantable medical device prior to implantation in the patient candidate; and
   implanting the preprogrammed implantable medical device in the patient candidate.

2. A method according to claim 1, wherein the customized programming parameters that specify patient-customized therapy are selected from the group comprising rate adaptive cardiac resynchronization, optimal AV delay, anti-oversensing, arrhythmia prediction, rate-adaptive pacing, and postural adaptive pacing.

3. A method according to claim 1, further comprising:
   collecting the physiological measures while the patient candidate is subject to a set of stressors.

4. A method according to claim 3, wherein the stressors are selected from the group comprising timed physical stressors, non-timed physical stressors, pharmacological stressors, sensory or autonomic stressors, or metabolic stressors.

5. A method according to claim 1, further comprising:
   establishing at least one of a reference baseline and a server profile comprising a representative physiological measures set.

6. A method according to claim 1, wherein the sensors further include sensors of an implanted medical device.

7. A method according to claim 6, wherein the implanted medical device is selected from the list comprising cardiac pacemakers, implantable cardioverter defibrillators, implantable cardiovascular monitors, and implantable therapeutic devices.

8. A method according to claim 1, wherein the sensors are external sensors selected from the set comprising electrocardiographic leads.

9. A method according to claim 1, wherein the physiological measures comprise at least one of cardiac and non-cardiac physiological measures.

10. A method according to claim 9, wherein the cardiac and non-cardiac physiological measures are selected from the set comprising patient activity score, posture, atrial electrical activity, ventricular electrical activity, cardiovascular pressures, cardiac output, oxygenation, pulmonary measures, body temperature, PR interval, QRS measures, QT interval, ST-T wave measures, potassium level, sodium level, glucose level, blood urea nitrogen and creatinine, acidity level, hematocrit, hormonal levels, cardiac injury chemical tests, myocardial blood flow, central nervous system injury chemical tests, and central nervous system blood flow.

11. A method according to claim 1, wherein the implantable medical device is selected from the group comprising a pacemaker, cardiac resynchronization therapy pacemaker, implantable cardioverter defibrillator, cardiac resynchronization therapy defibrillator, neurostimulation device, and implantable drug pump.

12. A method according to claim 1, further comprising:
preprogramming the therapy into a non-implantable medical device.

13. A method according to claim 12, wherein the non-implantable medical device comprises a drug infusion pump.

14. A computer-readable storage medium holding code for performing the method according to claim 1.

* * * * *